US00PP14776P3

(12) United States Plant Patent
Fleming et al.

(10) Patent No.: US PP14,776 P3
(45) Date of Patent: May 11, 2004

(54) HIBISCUS PLANT NAMED 'ROBERT FLEMING'

(50) Latin Name: *Hibiscus*
Varietal Denomination: Robert Fleming

(76) Inventors: David W. Fleming, 8101 S. 14th St., Lincoln, NE (US) 68512; Gretchen A. Zwetzig, 8101 S. 14th St., Lincoln, NE (US) 68512

( * ) Notice: Subject to any disclaimer, the term of this patent is extended or adjusted under 35 U.S.C. 154(b) by 205 days.

(21) Appl. No.: 09/950,213

(22) Filed: Sep. 10, 2001

(65) Prior Publication Data

US 2003/0097695 P1 May 22, 2003

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—W C Haas

(57) ABSTRACT

A new and distinct cultivar of winter hardy hibiscus plant named 'Robert Fleming' is the result of a unique hybridization. This new and distinct cultivar is characterized primarily as to novelty by its extreme cold hardiness to Zone 4, its ovate "Hydrangea-like" green leaves, its rich, large, dark red flowers that are very overlapping and ruffled, its short stature and compactness with vigorous growth potential, total refinement, and its floriferous nature from midsummer until frost.

3 Drawing Sheets

BACKGROUND OF THE NEW PLANT

The new plant of this invention is the result of a unique hybridization, with the breeding achievement being evidenced in the outstanding combination of characteristics exhibited by this new and distinct Hibiscus plant, which include: 'severely-cut' leaves of three to five (a) Refined and uniquely crinkled, "Hydrangea-like" ovate leaves of a medium green color with relatively smooth margins being densely distributed throughout the plant thereby complimenting the landscape;

(b) Very large flowers that are well-posed on the plant and outstanding for their deep red, thickly-textured petals with dark burgundy centers and an extremely campanulate nature;

(c)The plant being very floriferous with flowers that stay open at least one full day;

(d) The plant being short in stature, but vigorous with compact and uniform breaking action which gives it unique landscape utility; and (e) The plant being so hardy that it can consistently withstand winter temperatures of at least −30 degrees Fahrenheit.

SUMMARY OF THE INVENTION

'Robert Fleming' was the result of a 40 year breeding program. Its ancestry includes *Hibiscus moscheutos* and *Hibiscus coccineus*. More specifically, the plant resulted from multiple crossings of Fleming seedlings 'Ruffled Big Red' (*H. moscheutos*) with '12 A' (*H. coccineus*). Neither parent plant is patented. The seedling which most closely met all of the above named standards was selected.

This new plant first bloomed in the summer if 1989 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy Hibiscus plant greatly contributes to the market with its sheer beauty and utter refinement, its compact growth habit, its enhanced resistance to disease and insects, its stability through extremes in rain and drought, and its extreme hardiness.

BRIEF DESCRIPTION OF THE DRAWINGS

The flower, bud, foliage, and growth habit of the cultivar are shown in the attached illustrations.

More specifically, Photograph 1 shows a close-up of the flower.

Photograph 2 is a close-up of the foliage.

Photograph 3 depicts the growth habit of the cultivar, from the ground to the apex of the plant.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with the Dictionary of Color (Maerz and Paul), while general color recitations are consistent with ordinary American color terminology.

'Robert Fleming' has not been observed under all possible environment conditions. It is to be understood that the phenotype may vary significantly with variations in environment such as temperature, light intensity, and day length, and day length, without, however any difference in genotype of the plant. The following botanical characteristics and observations are gathered from the plant when grown under normal conditions in Lincoln, Nebr.

THE PLANT

Parentage:

*Seed parent.*—Seedling of '12A' (*H. coccineus*).

Pollen parent: Seedling of 'Ruffled Big Red' (*H. moscheutos*).

Origin: A selected seedling from a stated cross.

*Type of plant.*—Hardy, herbaceous perennial.

*Classification.*—Hybrid Hibiscus plant.

*Propagation.*—Relatively easy to propagate; holds its distinguishing characteristics through successive cuttings and division.

*Size.*—About 2½ feet tall and about 3 ft. wide.

*Form.*—Symmetrical annual growth from perennial roots.

*Flowering capability.*—Blooming not only from the apexes but from midbranch, as well; the plant regenerates blooms continuously.

*Habit.*—Upright and uniformly branched.

*Growth.*—Vigorous; medium and compact.

*Hardiness.*—Hardy to at least −30 degrees Fahrenheit.

*General health.*—Plant is very disease and pest resistent; sturdy through excessive drought, rain, or wind.

*Propagation.*—Relatively easy and fast rooting.

*Foliage.*— 1. Arrangement: Alternate. 2. Shape: Juvenile: Refined ovate leaf. Mature: Refined, ovate with smooth margins and creased leaf surfaces ("Hydrangea-like" in appearance), having acute apices. 3. Size: Mature leaf (petiole base to apex): Length is about 4½ inches (11 cm), width is about 3⅛ inches, 8 cm). 4. Color: Young leaves (upper side): 1 J, page 71, PLATE 24. Mature leaf: (upper side) 1 E, page 71, PLATE 24. Underside of leaves: 4 H, page 69, PLATE 23. 5. Surface texture: Semi-glabrous with deep crinkling over entire leaf surface. 6. Petiole length: About 1½ inches (4 cm). 7. Petiole color: Slightly brighter than 1 E, page 71, PLATE 24.

*Stems.*—The stems are stout at the base, becoming more slender toward the apices; coloration is consistent with the petiole.

THE FLOWER

Blooming period: Profuse from July until frost.

Flower diameter: Medium-large; about 7 inches (18 cm).

Borne: Singly in leaf axils, from midpoint of stems upward.

Bloom duration: Individual bloom lasts at least one full day.

Form: Campanulate; petals are very overlapping and ruffled.

Bud:

1. *Length.*—About 2 inches, (5½ cm) on the day before opening.
2. *Color.*—12 J, page 56, PLATE 56.
3. *Surface texture.*—Glabrous.
4. *Duration.*—One to two weeks.

Corolla:

1. *Petal character and dimensions.*—Campanulate and very overlapping. Length is about 3½ inches, (9 cm). Width is about 4¾ inches, (12 cm).
2. *Coloration.*—Medium red petals with darker center or eye (about 2 inches or 5 cm); eyezone is very glabrous. (a) Red petals: 6 H, page 7, PLATE 37. (b) Veination in petals: 6 H, page 39, PLATE 8. (c)Eye Zone: Slightly darker than 6-H, page 37, PLATE 7.
3. *Texture.*—Smooth.
4. *Substance.*—Thick.
5. *Shape.*—Campanulate, very overlapping, and ruffled.

Reproductive organs:

1. *Staminal column.*—Stamen along basal two-thirds. Stamen length: About 2 inches, (5 cm). Stamen color: 6 K, page 31, PLATE 4. Pollen color: 5 K, page 45, PLATE 11.
2. *Style.*—Terminates upper one-third of staminal coumn. Stigmatic lobe color: 6 L, page 37, PLATE 7.

Calyx: Connate at the base; about 1½ inches (3¾ cm) in length.

Stipules: None.

Epicalyx: Whorl of bracts.

1. *Shape.*—7 to 10 slender, sword-shaped bractlets.
2. *Length.*—About ¾ inches (2 cm).
3. *Color.*—6 Z, page 23, PLATE 23.

Penduncle:

1. *Length.*—About 1¾ inches, (4 cm).
2. *Strength.*—Stiff and sturdy.

GENERAL OBSERVATIONS

This plant, as a hybridized hardy Hibiscus, is valuable to the landscape market for its improvements in thicker-textured and uniquely colored and shaped flowers, refined "Hydrangea-like" leaves of green color, all-around vigor, good breaking action, more compact stature and adaptation to extreme environments, including the ability to consistently survive winter temperatures of at least −30 degrees Fahrenheit.

We claim:

1. A new and distinct cultivar of Hibiscus plant, as herein shown and described, characterized by its green, ovate "Hydrangea-type" crinkled foliage, its medium-sized and overlapping, bright red, ruffled flowers, its more compact size, its vigor and its hardiness.

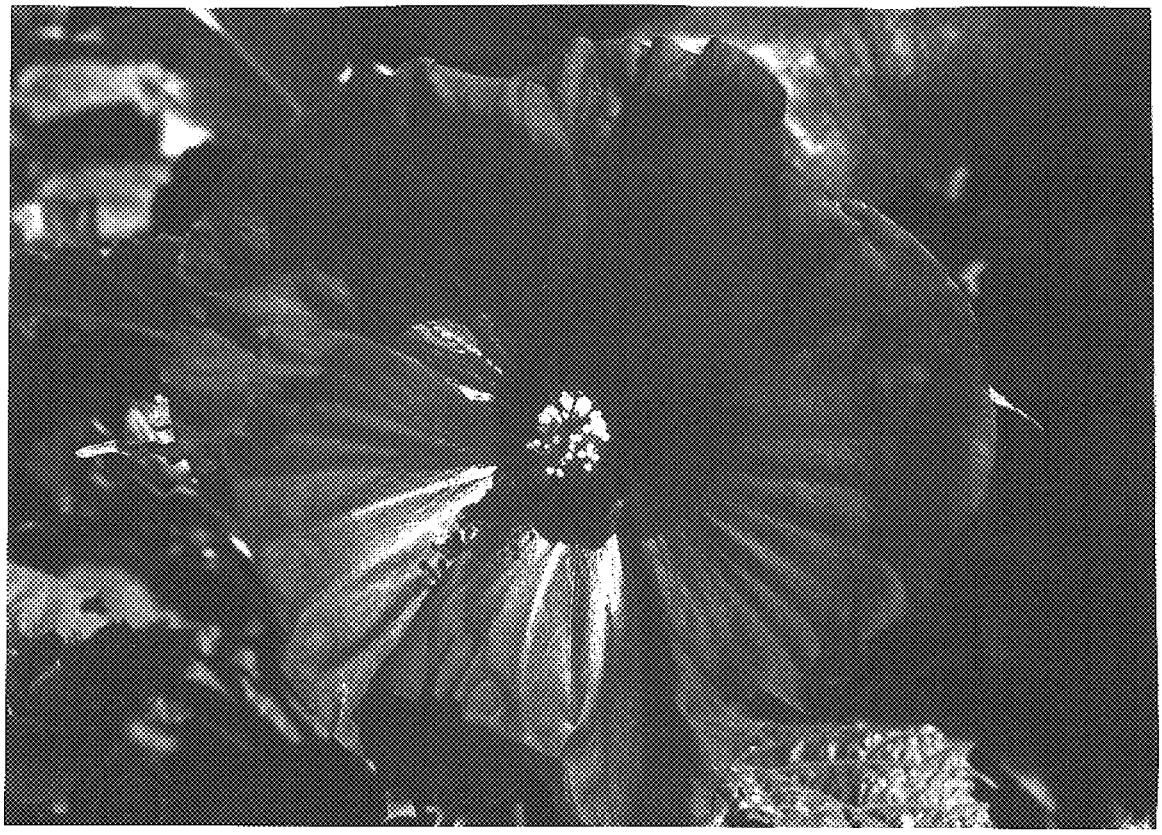

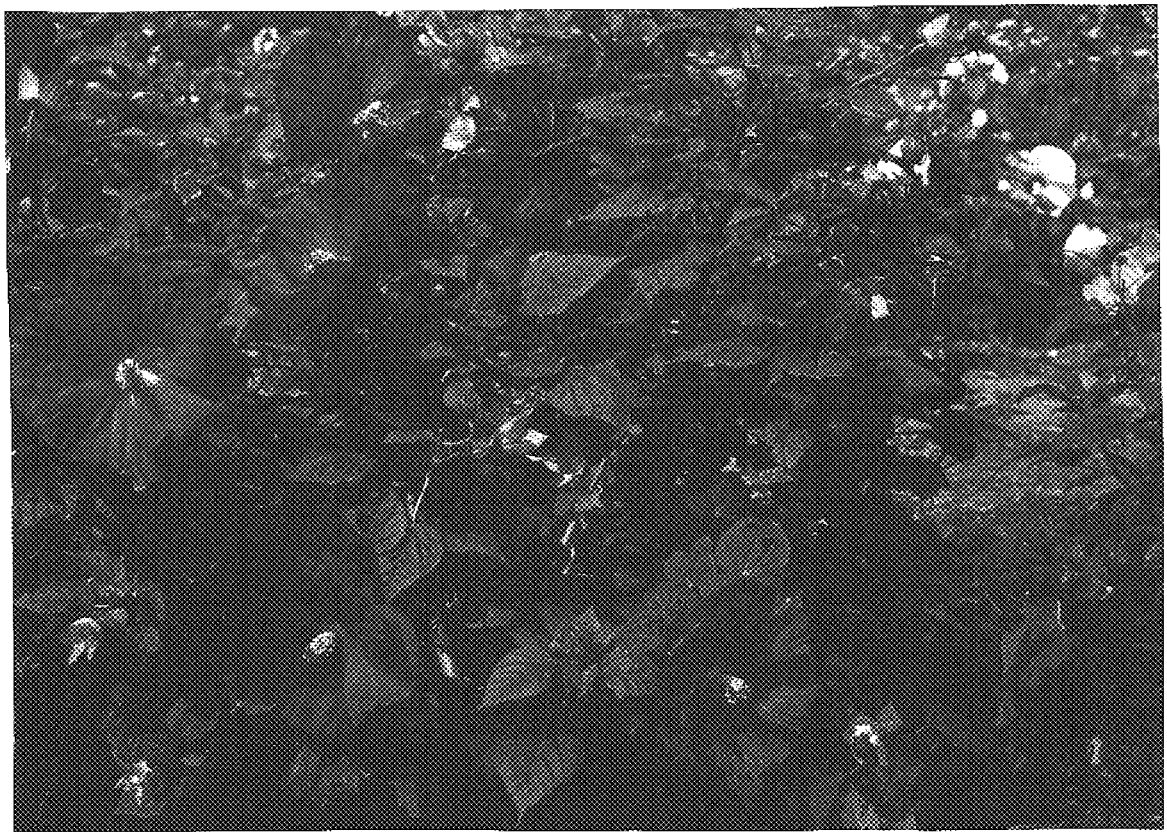

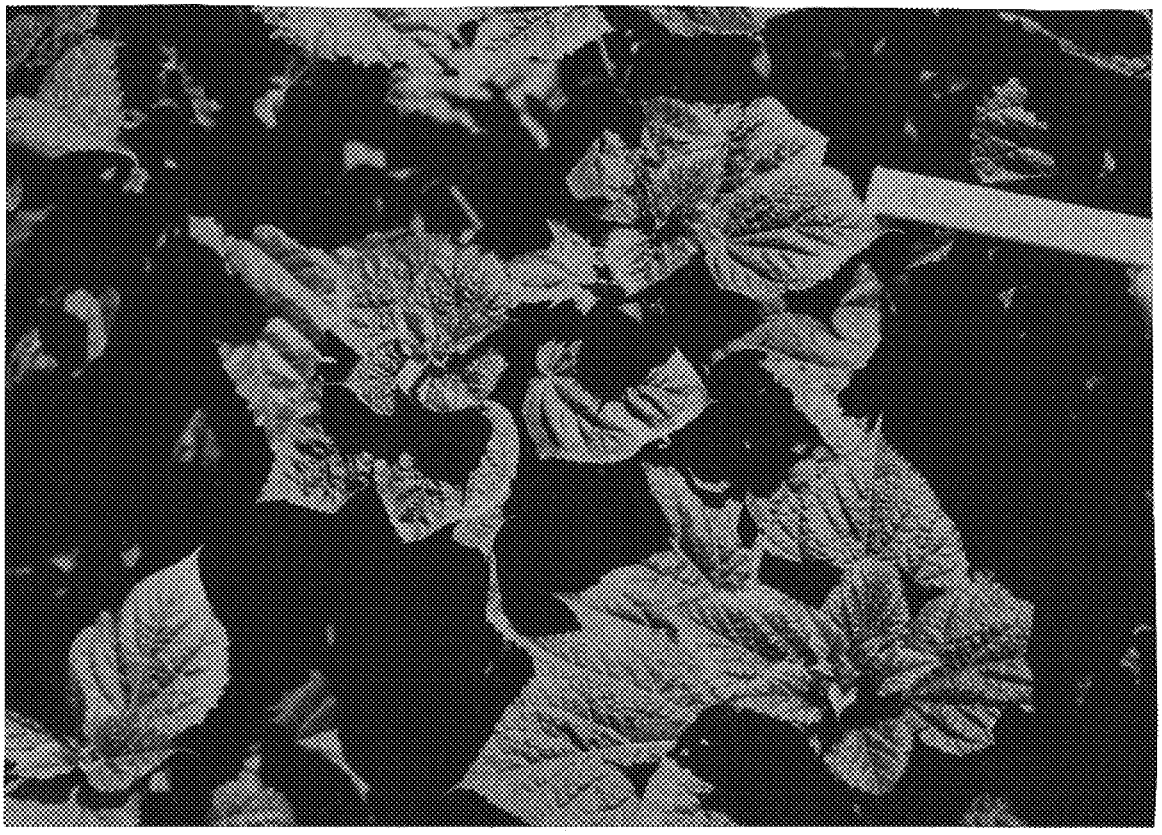

* * * * *